(12) United States Patent
Huttenloch et al.

(10) Patent No.: US 9,493,491 B2
(45) Date of Patent: Nov. 15, 2016

(54) METHOD OF SEPARATING ACIDS FROM CHEMICAL REACTION MIXTURES BY MEANS OF APOLAR AMINES

(71) Applicant: BASF SE, Ludwigshafen (DE)

(72) Inventors: Oliver Huttenloch, Ispringen (DE); Patrick Deck, Mannheim (DE); Holger Ganz, Ludwigshafen (DE); Michael Mauss, Neustadt (DE); Wolfgang Körnig, Leimen (DE); Michael Bock, Mannheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/148,430

(22) Filed: May 6, 2016

(65) Prior Publication Data
US 2016/0251384 A1 Sep. 1, 2016

Related U.S. Application Data

(62) Division of application No. 12/092,392, filed as application No. PCT/EP2006/066397 on Sep. 15, 2006, now Pat. No. 9,359,269.

(30) Foreign Application Priority Data

Nov. 8, 2005 (DE) .......................... 10 2005 053 540

(51) Int. Cl.
C07B 63/00 (2006.01)
C07F 9/22 (2006.01)

(52) U.S. Cl.
CPC ..................................... *C07F 9/224* (2013.01)

(58) Field of Classification Search
CPC ................................. C07B 63/00; C07F 9/224
See application file for complete search history.

(56) References Cited

U.S. PATENT DOCUMENTS

| 4,530,714 A * | 7/1985 | Kolc ........................ C05G 3/08 71/28 |
| 5,336,775 A | 8/1994 | Guberovic et al. |
| 5,770,771 A * | 6/1998 | Sulzer ..................... C01C 1/164 564/14 |
| 2004/0073035 A1* | 4/2004 | Maase ..................... C07C 45/50 546/187 |

FOREIGN PATENT DOCUMENTS

| EP | 0119487 A1 | 9/1984 |
| GB | 1398545 | 6/1975 |
| WO | WO-9101294 | 2/1991 |
| WO | WO-9831693 | 7/1998 |
| WO | WO-03062171 | 7/2003 |
| WO | WO-2005061416 | 7/2005 |

\* cited by examiner

*Primary Examiner* — Sudhakar Katakam
(74) *Attorney, Agent, or Firm* — Drinker Biddle & Reath LLP

(57) ABSTRACT

A process for the removal of acids from reaction mixtures, comprising at least one product of value which is sparingly soluble in water, by at least one unpolar amine as an auxiliary base, which includes: a) reacting the auxiliary base with the acid with formation of a salt; b) reacting the salt formed in step a) with a further base which accepts the acid with liberation of the auxiliary base and combines with the acid to be accepted from the auxiliary base to form a salt which is very readily soluble in water; c) extraction of the mixture obtained in step b) with water or an aqueous medium, wherein the salt of the further base dissolves in the aqueous phase and the product of value, or the solution of the product of value, in a suitable solvent and the auxiliary base form at least one separate nonaqueous phase; and d) removal by distillation of at least part of any solvent present from the at least one nonaqueous phase obtained in step c), to form two nonmiscible liquid phases.

5 Claims, No Drawings

METHOD OF SEPARATING ACIDS FROM CHEMICAL REACTION MIXTURES BY MEANS OF APOLAR AMINES

CROSS-REFERENCE TO RELATED APPLICATIONS

This application is a divisional of Ser. No. 12/092,392, filed May 1, 2008, which is incorporated by reference. Application Ser. No. 12/092,392 is a national stage application (under 35 U.S.C. §371) of PCT/EP2006/66397, filed Sep. 15, 2006, which claims benefit of German application 10 2005 053 540.2, filed Nov. 8, 2006. Both of which are incorporated herein by reference in their entirety.

DESCRIPTION

The present invention relates to a process for the improved removal of acids from polar reaction mixtures by means of unpolar amines. Furthermore, the invention relates to a process for the preparation of thiophosphoric triamides, to the thiophosphoric triamides obtainable by this process, and to the use of these thiophosphoric triamides as additive to urea-comprising mineral and/or organic-mineral fertilizers.

The skilled worker is frequently faced with the problem of scavenging acids liberated during a chemical reaction or removing acids from reaction mixtures. Examples of reactions in which acids are liberated in the course of the reaction are the silylation of alcohols or amines with halosilanes, the phosphorylation of amines or alcohols with phosphorus halides, the formation of sulfonic esters or sulfonic amides from alcohols or amines and sulfonyl chlorides or sulfonic anhydrides, and the formation of acyl compounds from acid halides or anhydrides and alcohols or amines.

Usually, it is necessary to bind these liberated acids with a base, with salt formation, in order to prevent secondary and subsequent reactions of the product of value or simply to remove the acid from the desired reaction product.

A process for removing acids from chemical reaction mixtures is described in WO 03/062171. This process of removing acids with the aid of ionic liquids allow typically unpolar products of value to be separated from acids in chemical reaction mixtures. A phase separation between the unpolar product of value and a polar ionic liquid, resulting from acid and added base, is exploited for this purpose. However, if the product of value is too polar in character, the phase separation between product of value and ionic liquid is hampered or made impossible. Polar products of value cannot be isolated by the strategy described in WO 03/062171.

It was an object of the present invention to identify a process for the removal of acids from chemical reaction mixtures with products of value which are sparingly soluble in water, allowing a technically simple liquid-liquid phase separation.

This object was achieved in accordance with the invention by employing an auxiliary base which is an unpolar amine for removing the acid.

The invention relates to a process for the removal of acids from reaction mixtures, comprising at least one product of value which is sparingly soluble in water, by means of at least one unpolar amine as auxiliary base, comprising the following steps:

a) reacting the auxiliary base with the acid with formation of a salt;

b) reacting the salt formed in step a) with a further base, which accepts the acid with liberation of the auxiliary base;

c) extraction of the mixture obtained in step b) with water or an aqueous medium, where the salt of the further base dissolves in the aqueous phase and the product of value, or the solution of the product of value, in a suitable solvent and the auxiliary base form at least one separate nonaqueous phase; and d) removal by distillation of the auxiliary base and/or at least part of the solvent which is optionally present from the at least one nonaqueous phase obtained in step c), it being possible for two nonmiscible liquid phases to form.

The invention furthermore relates to a process for the preparation of thiophosphoric triamides by reacting thiophosphoryl chloride with at least one primary or secondary amine in an inert solvent with the aid of at least one unpolar amine as auxiliary base, proceeding in accordance with the process according to the invention for the removal of acids from reaction mixtures, to the thiophosphoric triamides obtainable using this process and to the use of these thiophosphoric triamides as addition to urea-comprising mineral and/or organic/mineral fertilizers.

Phase separation in mixtures of liquids always occurs when two components of the mixture differ sufficiently with regard to their polarity, i.e. when one component is relatively polar, while the other component is relatively unpolar. A quantitative measure for assessing the systems in which this requirement is met is the respective activity coefficients of the one component in infinite dilution $\gamma^{\infty}$ in the respective other component. As described in the literature (H. R. Null "Phase Equilibrium in Process Design", Wiley Interscience, 1970), phase separation can only occur when $\gamma^{\infty} > 7.39$. All systems in which the above requirement is met should therefore permit phase separation and should thus be suitable for the claimed process.

As the result of the preferably anhydrous reaction of the starting materials, which are susceptible to hydrolyses, in the presence of the auxiliary base (base 1) and, if appropriate, in the presence of a solvent, the present invention gives a homogeneous or heterogeneous mixture of product of value and salt of base 1 and of the acid which has been formed or which is present (base 1•acid). The auxiliary base may be comprised in the reaction mixture or may be added later. The auxiliary base itself is advantageously liquid at temperatures at which the product of value does not undergo significant decomposition.

To separate this mixture, a further base (base 2) is added, which accepts the acid. This, in turn, liberates the unpolar base 1. Moreover, the added base 2 can engage in the formation, or further transformation, of the product of value, for example by the base undergoing a nucleophilic reaction (for example with ammonia, formation of phosphoric amides from phosphorus halides).

Bases which are suitable as base 2 are, in particular, those which are stronger than the base 1 used as auxiliary base. However, those which are likewise suitable as base 2 are those bases which, on the basis of the pK value, are formally weaker bases than the auxiliary base employed, when the proton transfer is influenced by secondary effects, such as the precipitation of a salt in anhydrous systems. Here, the proton transfer is driven by the salt's lattice energy which is released chloride, as the driving force for completion. This is the case for example when ammonia is used as base 2, with formation of solid ammonium chloride, since ammonia, with a $pK_B$ value of 4.77, is a weaker base than, for example, triethylamine (pK$_B$=3.25). In any case, base 2 must, together with the acid to be accepted from base 1, form a salt which is very readily soluble in water.

In a preferred embodiment, the nonaqueous mixture obtained in step c) of the process according to the invention, of product of value and auxiliary base (base 1), together with the solvent which is optionally present, forms a homogeneous phase. This is the case for example when product of value and auxiliary base are miscible with one another (case 1). In this case, the product of value is isolated by removing by distillation all of the auxiliary base and of the solvent which is optionally present.

However, in the presence of a suitable solvent, a homogeneous nonaqueous phase may form in step c) of the process according to the invention even when product of value and auxiliary base are not miscible with one another (case 2). In this case, the product of value can be isolated by removing by distillation some or all of the solvent, which results in two liquid phases which can be separated and of which one comprises the product of value, while the other comprises the auxiliary base. As an alternative, the auxiliary base may, again, be removed by distillation together with the solvent, with the product of value remaining as the residue.

In a further preferred embodiment, the nonaqueous mixture obtained in step c) of the process according to the invention, of product of value and auxiliary base (base 1) together with the solvent which is optionally present, is in biphasic form (case 3). This is the case for example when both the product of value and the solvent used are relatively polar so that they do not mix with the unpolar amine which is used in accordance with the invention as the auxiliary base. Here, product of value and auxiliary base can be separated immediately by phase separation; if required, the solvent which is optionally present may subsequently be removed by distillation from the product of value. As an alternative, the auxiliary base may, again, be removed by distillation together with the solvent, with the product of value remaining as the residue.

In step c) of the process according to the invention, the reaction mixture is extracted with water or an aqueous medium, so that the salt of the further base (base 2•acid), which is readily soluble in water, dissolves. Since the auxiliary base is unpolar in accordance with the invention, and the product of value too is only sparingly soluble in water, the aqueous solution of the salt of the further base (base 2•acid) forms a separate phase which can be removed readily. If required, an inert salt, for example an alkali metal halide or alkali metal sulfate, preferably sodium chloride, may be added to the water or aqueous medium used for the extraction in order to improve phase separation. The product of value is stable to hydrolysis under the conditions.

The solubility of the product of value in aqueous solution of base 2•acid is advantageously less than 10% by weight, preferably less than 2% by weight and very especially preferably less than 0.5% by weight.

The product of value which, in case 3 described above, forms a separate phase can be separated by phase separation not only from the aqueous salt solution, but also from base 1, which is present as a further separate phase. If, in case 2 described above, the product of value exists in the presence of a solvent, phase separation between the product of value and base 1 only takes place after removal of at least part of the volatile solvent.

Base 1 is removed and advantageously recirculated into the process.

The following schemes should clarify the principal difference between the processes of cases 1 and 2 described above, in comparison with case 3:

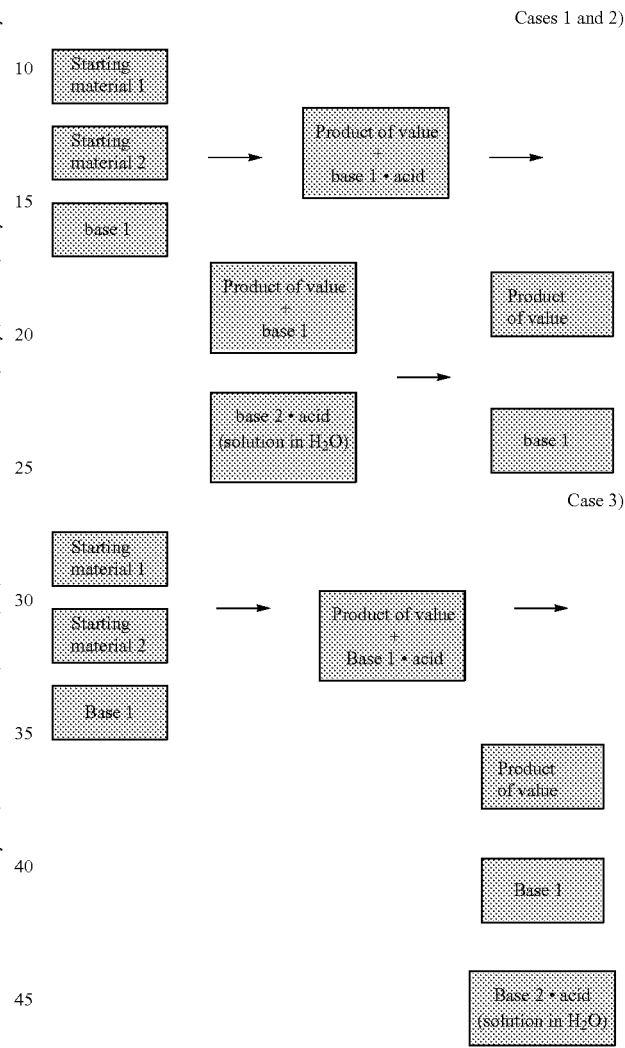

Explanations:
Starting material 1 or 2: susceptible to hydrolysis;
Base 1: unpolar amine (auxiliary base), insoluble in water, is recirculated into the process;
Base 1•acid: salt;
Base 2: polar (for example NaOH or NH$_3$);
Base 2•acid: salt, readily soluble in water, is dissolved.

As a rule, the product of value takes the form of polar organic or inorganic compounds, which are generated in the reactions listed hereinbelow by way of example.

The product of value can be present in solution in a suitable solvent. Suitable solvents are those which themselves do not react with the starting materials, which have good dissolving capacity for the starting materials and the product of value, and are preferably polar while simultaneously being sparingly soluble in water. An example of a suitable solvent is ethyl acetate. However, all other known, preferably polar, solvents which are sparingly soluble in water, such as esters and ketones, are also suitable. The solubility in water of the solvent is advantageously less than 20% by weight, preferably less than 10% by weight and most preferably less than 5% by weight.

In the removal by distillation of the solvent from the product of value, which may or may not be carried out, it is important that the boiling points of solvent and product of value are sufficiently different. As a rule, the boiling points of product of value and solvent should differ by at least 5° C., even better by at least 10° C. It is preferred that the solvent has a lower boiling point than the product of value.

Suitable chemical reactions which may be carried out with the process according to the invention are all reactions in which acids are liberated.

Examples of reactions in which the process according to the invention can be applied are alkylation reactions with alkyl or aralkyl halides, such as, for example, methyl chloride, methyl iodide, benzyl chloride, 1,2-dichloroethane or 2-chloroethanol, acylation reactions, i.e. reactions of acid halides and carboxylic anhydrides with any substrate, for example with alcohols or amines, silylation reactions, i.e. reactions with compounds which comprise at least one silicon-halogen bond, such as, for example, tetrachlorosilane ($SiCl_4$), dimethyldichlorosilane (($H_3C)_2SiCl_2$) or trimethylchlorosilane (($H_3C)_3SiCl$), phosphorylation and thiophosphorylation reactions, i.e. reactions with compounds which comprise at least one phosphorus-halogen bond, such as, for example, phosphorus trichloride ($PCl_3$), phosphorus pentachloride ($PCl_5$), phosphoryl chloride ($POCl_3$), thiophosphoryl chloride ($PSCl_3$), phosphonyl bromide ($POBr_3$), dichlorophenylphosphine or diphenylchlorophosphine, sulfurization reactions, i.e. sulfidation, sulfuration, sulfonation and sulfatization reactions, for example with sulfuryl chloride ($SO_2Cl_2$), thionyl chloride ($SOCl_2$), chlorosulfonic acid ($ClSO_3H$), sulfonyl halides such as p-toluenesulfonyl chloride, methanesulfonyl chloride or trifluoromethanesulfonyl chloride, or sulfonic anhydrides, elimination reactions in which a C=C double bond is formed with elimination of an acid, such as, for example, hydrogen chloride (HCl), hydrogen bromide (HBr), acetic acid or p-toluenesulfonic acid, or deprotonation reactions, in which an acidic hydrogen atom is abstracted from the auxiliary base.

Preferably among the abovementioned types of reactions are phosphorylation, thiophosphorylation, sulfurization and silylation reactions, with phosphorylation and thiophosphorylation reactions being especially preferred.

The acids to be removed as per the present invention can, for example, be Brönsted acids. The acids referred to as Brönsted acids are described in Hollemann-Wiberg, Lehrbuch der Anorganischen Chemie [Textbook of inorganic chemistry], 91$^{st}$-100$^{th}$ edition, Walter de Gruyter, Berlin New York 1985, p. 235 and p. 239.

As a rule, the compounds which are converted under silylation, phosphorylation, thiophosphorylation or sulfurization are, as a rule, those which have at least one free O—H, S—H or N—H bond, if appropriate after deprotonation by the auxiliary base.

Acids with which the bases can form salts are, for example, hydrogen iodide (HI), hydrogen fluoride (HF), hydrogen chloride (HCl), nitric acid ($HNO_3$), nitrose acid ($HNO_2$), hydrogen bromide (HBr), carbonic acid ($H_2CO_3$), hydrogen carbonate ($HCO_3^-$), methylcarbonic acid (HO(CO)$OCH_3$), ethylcarbonic acid (HO(CO)$OC_2H_5$), n-butyl-carbonic acid, sulfuric acid ($H_2SO_4^-$), hydrogen sulfate ($HSO_4$), methylsulfuric acid (HO($SO_2$)$OCH_3$), ethylsulfuric acid (HO($SO_2$)$OC_2H_5$), phosphoric acid ($H_3PO_4$), dihydrogen phosphate ($H_2PO_4^-$), formic acid (HCOOH), acetic acid ($CH_3COOH$), propionic acid, n- and isobutyric acid, pivalic acid, Para-toluenesulfonic acid, benzenesulfonic acid, benzoic acid, 2,4,6-trimethylbenzoic acid, mandelic acid, methanesulfonic acid, ethanesulfonic acid or trifluoromethanesulfonic acid, with hydrogen chloride, acetic acid, p-toluenesulfonic acid, methanesulfonic acid, 2,4,6-trimethylbenzoic acid and trifluoromethanesulfonic acid being preferred and with hydrogen chloride being especially preferred.

In accordance with the invention, the auxiliary bases employed are unpolar amines, in particular those which have no free O—H, S—H or N—H bond. Auxiliary bases which do not participate in the reaction as reactants are preferred.

Suitable auxiliary bases are, for example, tertiary amines of the formula (I)

$$NR^aR^bR^c \qquad (I),$$

are those in which $R^a$, $R^b$ and $R^c$ independently of one another are in each case $C_1$-$C_{18}$-alkyl, or are a $C_2$-$C_{18}$-alkyl, $C_6$-$C_{12}$-aryl or $C_5$-$C_{12}$-cycloalkyl which is optionally interrupted by one or more oxygen and/or sulfur atoms and/or one or more substituted or unsubstituted imino groups, or are a radical of a five- to six-membered heterocycle containing oxygen, nitrogen and/or sulfur atoms, or two thereof together form, together with the nitrogen atom to which they are bonded, an unsaturated, saturated or 5- to 7-membered aromatic ring which is optionally interrupted by one or more oxygen and/or sulfur atoms and/or one or more substituted or unsubstituted imino groups, it being possible for the abovementioned radicals to be substituted in each case by still further aryl, alkyl, aryloxy and alkyloxy groups, halogen atoms and/or radicals of heterocycles, and to comprise still further hetero atoms and/or functional groups. Here, the term aryl group represents an aromatic hydrocarbon radical having 6 to 12 C atoms, alkyl group represents a branched or unbranched saturated hydrocarbon radical having 1 to 18 C atoms, aryloxy group represents a radical which is derived from an aromatic phenol having 6 to 12 C atoms, alkyloxy group represents a radical which is derived from an aliphatic monoalcohol having 1 to 18 C atoms, and halogen represents the elements fluorine, chlorine, bromine and iodine. Heterocycles are pyrrolidine, piperidine, morpholine, furan, thiophene, pyrrole, imidazole, pyrazole, oxazole, isoxazole, thiazole, isothiazole, oxadiazole, thiadiazole, triazole, quinoline, isoquinoline, pyridine, pyrimidine, pyrazine, pyridazine or s-triazine. Further hetero atoms are nitrogen, oxygen, sulfur or phosphorus, and functional groups are carbonyl, carboxyl, ester, cyano or nitro groups.

$R^a$, $R^b$ and $R^c$ are preferably independently of one another in each case $C_1$-$C_{18}$-alkyl, $C_6$-$C_{12}$-aryl or $C_5$-$C_{12}$-cycloalkyl and especially preferably $C_1$-$C_{18}$-alkyl, it being possible for the abovementioned radicals to be substituted in each case by still further aryl, alkyl, aryloxy and/or alkyloxy groups, halogen atoms and/or radicals of heterocycles, and to comprise still further hetero atoms and/or functional groups.

Preferred meanings for the radicals $R^a$, $R^b$ and $R^c$ are methyl, ethyl, n-propyl, isopropyl, n-butyl, sec-butyl, tert-butyl, n-pentyl (n-amyl), 2-pentyl (sec-amyl), 3-pentyl, 2,2-dimethylprop-1-yl (neopentyl), n-hexyl, n-heptyl, n-octyl, isooctyl, 2-ethylhexyl, 1,1-dimethylpropyl, 1,1-dimethylbutyl, benzyl, 1-phenylethyl, 2-phenylethyl, α,α-dimethylbenzyl, phenyl, tolyl, xylyl, α-naphthyl, β-naphthyl, cyclopentyl or cyclohexyl.

If two of the radicals $R^a$, $R^b$ and $R^c$ form a chain, this may be, for example, 1,4-butylene or 1,5-pentylene, where these two radicals together with the nitrogen atom linking them form a pyrrolidinyl or piperidinyl radical.

Examples of the tertiary amines are trimethylamine, triethylamine, diethylmethylamine, diethyl-n-propylamine, diethyl-n-butylamine, diethyl-tert-butylamine, diethyl-n-pentylamine, diethyihexylamine, diethyloctylamine, diethyl-(2-ethylhexyl)amine, tri-n-propylamine, di-n-propylmethylamine, di-n-propylethylamine, di-n-propylbutylamine, di-n-propyl-n-pentylamine, di-n-propylhexylamine, di-n-propyloctylamine, di-n-propyl-(2-ethylhexyl)amine, diisopropylmethylamine, diisopropylethylamine, diisopropyl-n-propylamine, diisopropylbutylamine, diisopropylpentylamine, diisopropylhexylamine, diisopropyloctylamine, diisopropyl-(2-ethylhexyl)amine, tri-n-butylamine, di-n-butylmethylamine, di-n-butylethylamine, di-n-butyl-n-propylamine, di-n-butyl-n-pentylamine, di-n-butylhexylamine, di-n-butyloctylamine, di-n-butyl-(2-ethylhexyl)amine, N-methylpyrrolidine, N-ethylpyrrolidine, N-n-propylpyrrolidine, N-isopropylpyrrolidine, N-n-butylpyrrolidine, N-sec-butylpyrrolidine, N-tert-butylpyrrolidine, N-n-pentylpyrrolidine, N,N-dimethylcyclohexylamine, N,N-diethylcyclohexylamine, N,N-di-n-butylcyclohexylamine, N-methylpiperidine, N-ethylpiperidine, N-n-propylpiperidine, N-isopropylpiperidine, N-n-butylpiperidine, N-sec-butylpiperidine, N-tert-butylpiperidine, N-n-pentylpiperidine, N-methylmorpholine, N-ethylmorpholine, N-n-propylmorpholine, N-isopropylmorpholine, N-n-butylmorpholine, N-sec-butylmorpholine, N-tert-N-n-pentylmorpholine, N-benzyl-N-methylaniline, N-benzyl-N-ethylaniline, N-benzyl-N-n-propylaniline, N-benzyl-N-isopropylaniline, N-benzyl-N-n-butylaniline, N,N-dimethyl-p-toluidine, N,N-diethyl-p-toluidine, N,N-di-n-butyl-p-toluidine, dimethylbenzylamine, diethylbenzylamine, di-n-propylbenzylamine, di-n-butylbenzylamine, dimethylphenylamine, diethylphenylamine, di-n-propylphenylamine and di-n-butylphenylamine.

The auxiliary bases are preferably tertiary amines, in particular trialkylamines.

The following are preferred: trimethylamine, triethylamine, diethylmethylamine, diethyl-n-propylamine, diethyl-n-butylamine, tri-n-propylamine, di-n-propylmethylamine, di-n-propylethylamine, tri-n-butylamine, di-n-butylmethylamine, di-n-butylethylamine.

Especially preferred tertiary amines are triethylamine, tri-n-propylamine and tri-n-butylamine.

The abovementioned auxiliary bases can be employed individually or in mixtures with one another in order to solve the problem of the invention.

The auxiliary base is advantageously liquid at temperatures at which the product of value does not undergo decomposition significantly.

For the purposes of the present invention, "no significant decomposition of the product of value" means that less than 10 mol % per hour, preferably less than 5 mol %/h, especially preferably less than 2 mol %/h and very especially preferably less than 1 mol %/h of product of value undergo decomposition.

As a rule, the melting points of the especially preferred auxiliary bases are less than 50° C., especially preferably less than 25° C. and very especially preferably less than 10° C.

In the removal by distillation of the auxiliary base from the product of value, which may or may not be carried out, it is important that the boiling points of auxiliary base and product of value are sufficiently different. As a rule, the boiling points of product of value and auxiliary base should differ by at least 5° C., even better by at least 10° C. It is preferred that the auxiliary base has a lower boiling point than the product of value.

According to the invention, the auxiliary bases employed are unpolar and are therefore sparingly soluble in water at room temperature with a solubility in water of less than 10% by weight, preferably less than 2% by weight and very especially preferably less than 0.5% by weight.

The auxiliary base should be chosen in such a way that it has no decomposing effect on the product of value, either in the form of the salt or in the form of the free base (after addition of base 2).

To accept the acid from the salt base 1•acid, a further base (base 2) is employed in accordance with the invention.

Such bases may comprise any desired groups such as, for example, OH, $NH_2$ or alkoxide groups. As has already been detailed further above, they may be stronger than base 1. If, in contrast, they are weaker bases than base 1, such as ammonia in relation to tertiary amines, the reaction of base 2 with the salt of base 1 to give the salt of base 2 with liberation of base 1 must have a distinctly negative reaction enthalpy.

Examples of added further bases (base 2) are ammonia, inorganic hydroxides, alkoxides, inorganic amides, inorganic carbonates, organic amidine bases such as 1,8-diazabicyclo[5.4.0]undec-7-ene (DBU) and 1,5-diazabicyclo[4.3.0]non-5-ene (DBN), or polar amines which are readily soluble in water, such as, for example, oligoethylenimine (Polymin®, BASF Aktiengesellschaft).

The following are preferably employed: sodium hydroxide (NaOH), potassium hydroxide (KOH), calcium hydroxide ($Ca(OH)_2$), lime water, sodium carbonate ($Na_2CO_3$), sodium hydrocarbonate ($NaHCO_3$), potassium carbonate ($K_2CO_3$), ammonia ($NH_3$), sodium methoxide. Sodium hydroxide and ammonia are especially preferably employed.

Here, it is not possible in accordance with the invention to add base 2 to the reaction mixture at the beginning since base 2 would react with the starting materials.

Water or an aqueous medium are employed for converting the salt base 2•acid into an aqueous solution. The aqueous medium can be any type of aqueous mixture in which water is present in an amount of more than 1% by weight, preferably more than 50% by weight, especially preferably more than 90% by weight.

In a further embodiment of the invention, base 2 is already added as an aqueous solution in step b) of the process according to the invention.

The compounds employed for the process according to the invention are advantageously employed in the following molar ratios:

The auxiliary base (base 1) is used for example in an amount of from 0.5 to 3 mol equivalents, preferably 0.8 to 1.5 mol equivalents, in each case based on the starting material which is present in a smaller molar amount.

The auxiliary base (base 2) is used for example in an amount of from 0.5 to 10 mol equivalents, preferably 1.0 to 3 mol equivalents, in each case based on the starting material which is present in a smaller molar amount.

Water should be employed in an amount of from 50 to 5000% by weight, preferably 100 to 1000% by weight, in each case based on the salt of the further base.

The procedure of the reaction is not limited and can be carried out according to the invention with scavenging of the acids which have been liberated or added, batchwise or continuously and in the air or under a protective gas atmosphere.

The reaction between the starting materials in the presence of the auxiliary base usually proceeds at temperatures of from −70° C. to +150° C., preferably from −30° C. to +50° C. The reaction with the further base (base 2) usually likewise proceeds at temperatures of from −70° C. to +150° C., preferably from −30° C. to +50° C. The extraction of the salt base 2•acid with water or an aqueous medium is preferably carried out by dissolving the salt at temperatures of from −10° C. to +100° C., especially preferably from −5° C. to +50° C. The two separated nonaqueous liquid phases in cases 2 and 3 described above, auxiliary base on the one hand and product of value on the other hand, are formed above the melting point of the product of value. The temperature range for the phase separation is preferably between 0° C. and 150° C., especially preferably between 15° C. and 100° C.

All process steps can be carried out under atmospheric pressure, under pressure or else under reduced pressure. In the presence of gaseous reactants or gaseous bases, the pressure is preferably less than 50 bar.

The auxiliary base which has been removed from the process can be recirculated into the process in a manner known to the skilled worker.

If required, the auxiliary base can be washed with water or aqueous sodium chloride or sodium sulfate solution and then dried, for example by removing any water which may be present with the aid of an azeotropic distillation using benzene, toluene, xylene, butanol or cyclohexane.

If required, the auxiliary base can be distilled before it is reused.

The process according to the invention allows the successful removal of acids from chemical reaction mixtures with products of value which are sparingly soluble in water. By reaction with a further base (base 2), the salt of the unpolar auxiliary base (base 1) is reacted, with liberation of the auxiliary base, to give the salt of base 2, which salt is considerably more readily soluble in water than the salt of the unpolar auxiliary base.

Since the product of value, too, is only sparingly soluble in water, the salt of base 2 can be separated by a technically simple process of a liquid-liquid phase separation following extraction with water or an aqueous medium. The technically complicated handling of solids can thereby be dispensed with. The auxiliaries can be worked up in absence of the product of value, so that the latter is less contaminated.

The process according to the invention can successfully be employed in all of the reactions which have been described further above, in particular in the preparation of (thio)phosphoric acid derivatives such as amides, esters and mixed species.

Accordingly, the invention further relates to the preparation of thiophosphoric triamides by reacting thiophosphoryl chloride with at least one primary or secondary amine using the process described above.

It is known that thiophosphoric triamides are hydrolyzed relatively readily to give the corresponding phosphoric triamides. In the presence of moisture, thiophosphoric triamides and their corresponding phosphoric triamides are, as a rule, present as a mixture with one another. Herein the term "thiophosphoric triamide" therefore refers not only to the pure thiophosphoric triamides, but also to their mixtures with the corresponding phosphoric triamides.

In accordance with the invention, thiophosphoric triamides are prepared by reacting thiophosphoryl chloride with at least one primary or secondary amine in an inert solvent with the aid of at least one unpolar amine as the auxiliary base, comprising the following steps:

a) reaction of the auxiliary base with the halogen chloride formed during the reaction, with formation of a chloride salt;
b) reaction of the chloride salt formed in step a) with ammonia, which accepts the hydrogen chloride with liberation of the auxiliary base;
c) extraction, of the mixture obtained in step b) with water or an aqueous medium, where the ammonium chloride formed dissolves in the aqueous phase and the solution of the product of value in the inert solvent and the auxiliary base form at least one separate nonaqueous phase; and
d) removal by distillation of the auxiliary base and/or of at least some of the inert solvent from the at least one nonaqueous phase obtained in step c), it being possible for two nonmiscible liquid phases to be formed.

At least one primary or secondary amine is employed for reacting the thiophosphoryl chloride.

These compounds are advantageously compounds of the general formula (II)

In this formula, $R^1$ and $R^2$ independently of one another are hydrogen, alkyl, alkenyl, cycloalkyl, aryl or hetaryl.

The alkyl radicals preferably have 1 to 20 C atoms, especially preferably 3 to 5 C atoms, the alkenyl radicals preferably have 2 to 20 C atoms, especially preferably 3 to 6 C atoms, the cycloalkyl radicals preferably have 3 to 20 C atoms, especially preferably 5 to 7 C atoms, and the aryl radicals preferably have 6 to 10 C atoms. Aryl is preferably phenyl or naphthyl.

Hetaryl is a radical derived, for example, from furan, thiophene, pyrrole, imidazole, pyrazole, oxazole, isoxazole, thiazole, isothiazole, oxadiazole, thiadiazole, triazole, quinoline, isoquinoline, pyridine, pyrimidine, pyrazine, pyridazine or s-triazine. Especially preferred hetaryl radicals are derived from furan, thiophene and imidazole.

In an advantageous embodiment, the two radicals of the amino group together form an alkylene or alkenylene chain which, together with the nitrogen atom linking them, forms a 3- to 6-membered, preferably 5-membered, ring system which, if appropriate, comprises one or more further hetero atoms chosen from the group consisting of oxygen, nitrogen and sulfur.

The substituents R1 and R2 can additionally have attached to them one or more radicals such as, for example, halogen, cyano, $C_1$- to $C_6$-alkylthio, $C_1$- to $C_6$-alkoxy, $C_6$- to $C_{12}$-aryl, $C_1$- to $C_6$-(di)alkylamino, to $C_6$-alkoxycarbonyl, aryloxycarbonyl, carbamoyl, hydroxyl, amino, sulfo or nitro. The substituents $R^1$ and $R^2$ especially preferably comprise halogen or amino groups.

Alkylamines are preferably employed, especially preferably n-butylamine and/or n-propylamine.

The primary or secondary amines can be used individually or as a mixture with one another, for example a mixture of two or more alkylamines, a mixture of two or more arylamines or a mixture of in each case one or more alkylamine(s) and arylamine(s). An advantageous mixture is n-butylamine and n-propylamine with n-butylamine contents of 40 to 99% by weight. An n-butylamine content of from 60 to 80% by weight is preferred and a content of 72 to 78% by weight is especially preferred.

The amines are preferably used in a molar ratio of from 0.9 to 1.1 mol per mole of thiophosphoryl chloride, especially preferably from 0.95 to 1.05 mol of amine per mole of thiophosphoryl chloride. In an advantageous embodiment, approximately 1 mol of amine is employed per mole of thiophosphoryl chloride.

In accordance with the invention, the thiophosphoryl chloride is reacted in an inert polar solvent.

Solvents which can be employed in accordance with the invention are all known inert polar solvents. Examples of solvents which can be used are: acetone, methyl ethyl ketone, isobutyl methyl ketone, diethyl ketone, diethyl ether, di-n-butyl ether, tert-butyl methyl ether, tert-butyl ethyl ether, tetrahydrofuran, dioxane, acetic esters such as ethyl acetate, methyl acetate, propyl acetate, butyl acetate or 2-ethylhexyl acetate, dimethylformamide, dimethyl sulfoxide, acetonitrile, diethyl phthalate, dioctyl adipate, chloroform, dichloromethane, methylchloroform or mixtures of these. It is preferred to employ ethyl acetate.

The inert polar solvents can be employed alone or as a mixture of two or more thereof.

The process according to the invention is preferably used for the preparation of N-alkylthiophosphoric triamides, for example N-n-butylthiophosphoric triamide or N-n-propylthiophosphoric triamide.

To this end, thiophosphoryl chloride and a primary alkylamine, for example n-butylamine, are reacted in molar ratios of preferably 0.9 to 1.1 mol of amine per mole of thiophosphoryl chloride in an inert solvent, for example ethyl acetate. The auxiliary base used is a trialkylamine, for example tri-n-butylamine, which is reacted to give the tri-n-butylamine hydrochloride. In a second reaction step, the N-alkylthiophosphoryl dichloride which has been formed in the first reaction is reacted with ammonia at temperatures of between preferably −20° C. and 50° C. to give the desired product N-alkylthiophosphoric triamide. In parallel with, and independently of, the second reaction step, ammonia acts as base 2 and accepts the hydrogen chloride from the trialkylamine hydrochloride with formation of ammonium chloride.

Ammonia is preferably used in a molar ratio of from 2 to 15 mol per mole of thiophosphoryl chloride, especially preferably 2.1 to 10 and especially preferably 2.2 to 40 7 mol of ammonia per mole of thiophosphoryl chloride. In an advantageous embodiment, approximately 4 to 6 mol of ammonia are employed per mole of thiophosphoryl chloride.

The extraction of the reaction mixture with sufficient amounts of water in step c) of the process according to the invention gives rise to an aqueous solution of ammonium chloride and an organic phase comprising the inert solvent, trialkylamine and N-alkylthiophosphoric triamide. As a rule, the amount of water employed for the extraction is in the range of from approximately 10 to approximately 100 mol of water per mole of N-alkylthiophosphoric triamide, preferably in the range of from 15 to 50 mol of water per mole of N-alkylthiophosphoric triamide.

The extraction may be carried out in one or more steps and may be performed both continuously and batchwise. It is preferred to perform a multi-step extraction, for example in a mixer-settler arrangement which is known to the skilled worker and which consists of dispersing steps and phase separators, or in a pulsed-stirred extraction column. The number of theoretical plates should amount to 1 to 10, preferably 3 to 5. To lose as little product of value as possible, it is advantageous to subject the aqueous phase from the extraction with the solvent ethyl acetate to a back extraction in the same apparatus. Some of the water used for the extraction may advantageously be added to the reaction mixture in a separate reactor or a mixing device even before the actual extraction apparatus, in order to allow sufficient time for the dissolution of the 20 ammonium chloride in the aqueous phase.

After removal of the inert solvent by distillation, a two-phase liquid-liquid mixture (case 2, see above) of a trialkylamine phase and an N-alkylthiophosphoric triamide phase is formed within a temperature window of between 15° C. and 100° C.

As an alternative, it is also possible to evaporate almost all of the trialkylamine together with the inert solvent, with the product of value N-alkylthiophosphoric triamide remaining as a residue. This evaporation may be performed for example with a thin-film evaporator, multi-phase coiled-tube evaporator, climbing film evaporator or short path evaporator with a short residence time, immediately after the extraction, whereby the thermal stress of the product of value is kept at a minimum. If a longer residence time is acceptable, it is also possible to employ falling-film evaporators or long-tube evaporators may also be employed. In a preferred embodiment, a two-step evaporation is carried out in a thin-film evaporator with a total residence time in both steps of less than 2 minutes. The pressure in the first thin-film evaporator step is 50 to 150 mbar, preferably 60 to 90 mbar. The temperature in the first thin-film evaporator step is 80 to 150° C., preferably 100 to 130° C. The pressure in the second evaporator step is 0.1 to 20 mbar, preferably less than 2 mbar, and the temperature is 80 to 140° C., preferably 90 to 100° C. Since the ammonium chloride has been extracted previously in accordance with the invention, this evaporation causes no precipitations or solids formation whatsoever, which would make the operation of the apparatus more difficult.

The vapors forming during evaporation may be condensed and subsequently processed in a solvent column, for example a dividing-wall column, and be circulated into the process.

The invention furthermore relates to thiophosphoric triamides which are obtainable by the above-described process.

The thiophosphoric triamides which are obtainable by the process according to the invention preferably have a low residual ammonium chloride content. In a specially preferred embodiment of the invention, the thiophosphoric triamides obtainable by the process according to the invention have an ammonium chloride content of <500 ppm (w/w), very especially preferably of <100 ppm (w/w), in each case based on the thiophosphoric triamide.

In a further preferred embodiment of the invention, the thiophosphoric triamides obtainable by the process according to the invention have a combined residual content of inert solvent and auxiliary base of <1% by weight, especially preferably of <0.5% by weight, in each case based on the thiophosphoric triamide.

Thiophosphoric triamides, specifically N-n-butylthiophosphoric triamide (NBPT) or N-n-propylthiophosphoric triamide, are potent urease inhibitors which are employed in urea-based fertilizer compositions. Such urease inhibitors can be used for improving the efficiency of the urea fertilization since losses as the result of the urease-catalyzed degradation of urea in the soil are reduced. (Trenkel, M. E., "Controlled-Release and Stabilized Fertilizers in Agriculture", IFA 1997, ISBN: 2-9506299-0-3).

The invention further relates to the use of the thiophosphoric triamides which have been prepared in accordance with the process according to the invention as additive to urea-comprising mineral and/or organic/mineral fertilizers.

The invention is further illustrated by the following examples.

EXAMPLES

Example 1

Preparation of N-n-Butylthiophosphoric Triamide (NBPT) in Accordance with Case 2

423.5 g (2.5 mol) of thiophosphoryl chloride and 937.5 g of ethyl acetate were initially introduced. A mixture of 193.7 g (2.65 mol) of n-butylamine, 440.2 g (2.375 mol) of tributylamine and 316.6 g of ethyl acetate were added dropwise to this mixture at not more than 30° C. The temperature was maintained at 30° C. by cooling. This gave a clear solution. Stirring of the mixture was continued for 3 hours at room temperature.

Thereafter, ammonia at 0° C. was passed in until the uptake was complete. The ammonia uptake amounted to 5 to 6 mol equivalents. This gave a fluid suspension of precipitated ammonium chloride and N-n-butylthiophosphoric triamide as product of value, dissolved in ethyl acetate. The mixture was warmed to room temperature. 1406 g of water were added and stirring was continued at room temperature. During this process, all of the ammonium chloride dissolved.

The resulting clear phases were separated, and the organic phase was concentrated. After most of the ethyl acetate had been removed, a top phase of tributylamine and a bottom phase of liquid NBPT were formed at approximately 60° C. The phases were separated, and an NBPT melt was obtained and was treated, at 50° C., with 1200 g of water with a temperature of 50° C. The mixture was cooled, with stirring, during which process the NBPT separated out as a solid. The solid was removed by filtration and dried.

This gave 364.8 g of product with an NBPT content of 76% by weight (yield 66%).

Example 2

Preparation of N-n-Butylthiophosphoric Triamide (NBPT) in Accordance with Case 3

In a reaction proportioning pump, a stream of 68 ml/h thiophosphoryl chloride was combined with a stream of 876 ml/h of a mixture of n-butylamine and tri-n-butylamine (0.079:1 w/w) with a residence time of 13 s, while cooling with ice-water. The discharge from the pump was passed for 1 hour into a reactor into which tributylamine (approx. 10:1 vol feed:vol $Bu_3N$) had been introduced, while continuously passing in an excess of ammonia gas at 0° C. The resulting milky-white suspension was treated with 306 g of water and heated to 40° C. A three-phase system of aqueous bottom phase, middle phase of product of value and tributylamine phase at the top was formed.

We claim:

1. A process for the preparation of thiophosphoric triamides by reacting thiophosphoryl chloride with at least one primary or secondary amine in an inert solvent with the aid of at least one unpolar amine as an auxiliary base, comprising the following steps:
   a) reacting the auxiliary base with the hydrogen chloride formed during the reaction, with formation of a chloride salt;
   b) reacting the chloride salt formed in step a) with ammonia, which accepts the hydrogen chloride with liberation of the auxiliary base;
   c) extracting the mixture obtained in step b) with water or an aqueous medium, wherein ammonium chloride formed dissolves in the aqueous phase and the solution of the product of value in the inert solvent and the auxiliary base form at least one separate nonaqueous phase; and
   d) removing by distillation of at least some of the inert solvent from the at least one nonaqueous phase obtained in step c), to form two nonmiscible liquid phases.

2. The process according to claim 1, wherein the auxiliary base is a tertiary amine.

3. The process according to claim 1, wherein the auxiliary base is triethylamine, tri-n-propylamine or tri-n-butylamine.

4. The process according to claim 1, wherein the acid is liberated during the course of a phosphorylation or thiophosphorylation reaction.

5. The process according to claim 1, wherein the auxiliary base is separated off and recirculated into the process.

* * * * *